(12) United States Patent
Flint et al.

(10) Patent No.: US 7,041,501 B2
(45) Date of Patent: May 9, 2006

(54) METHODS OF SCREENING FOR TOXICITY OF TEST COMPOUNDS

(75) Inventors: Oliver P. Flint, Newtown, PA (US); Frederic Moulin, Newtown, PA (US); Stephen K. Durham, Langhorne, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 357 days.

(21) Appl. No.: 10/285,093

(22) Filed: Oct. 31, 2002

(65) Prior Publication Data

US 2003/0113708 A1    Jun. 19, 2003

Related U.S. Application Data

(60) Provisional application No. 60/336,509, filed on Oct. 31, 2001.

(51) Int. Cl.
*C12N 5/00* (2006.01)
(52) U.S. Cl. .................. 435/370; 435/25; 435/325; 435/361
(58) Field of Classification Search ................ 435/370, 435/366, 325, 25
See application file for complete search history.

(56) References Cited

U.S. PATENT DOCUMENTS

| | | | |
|---|---|---|---|
| 5,164,313 A | 11/1992 | Gelboin et al. | |
| 5,342,777 A | 8/1994 | Cole et al. | |
| 5,356,806 A | 10/1994 | Harris et al. | |
| 5,506,131 A | 4/1996 | Harris et al. | |
| 5,529,920 A | 6/1996 | Cole et al. | |
| 5,614,505 A * | 3/1997 | Gmeiner et al. | 514/50 |
| 5,660,986 A | 8/1997 | Harris et al. | |
| 5,665,589 A | 9/1997 | Harris et al. | |
| 5,759,782 A * | 6/1998 | Pastan et al. | 435/6 |
| 5,869,243 A | 2/1999 | Jauregui et al. | |
| 6,214,803 B1 * | 4/2001 | Kuo et al. | 514/26 |
| 6,852,845 B1 * | 2/2005 | Rothberg et al. | 536/23.1 |
| 2004/0010809 A1 * | 1/2004 | Wolf et al. | 800/3 |

OTHER PUBLICATIONS

Pfeifer A.M. et al., Proc. Natl.Acad.Sci., USA, vol. 90, pp. 5123-5127 (1993).
Evans, W.E. and Relling M.V., Science, vol. 286 (5439), pp. 487-491 (1999).
Schiller et al., Toxicology in Vitro, vol. 6 No. 6, pp. 575-578 (1992).
Leeder et al., Drug Metabolite Toxicity Assessed in Human Lymphocytes With a Purified, Reconstituted Cytochrome P-450 System[1], Feb. 22, 1988, pp. 956-962.

* cited by examiner

*Primary Examiner*—Leon B. Lankford, Jr.
(74) *Attorney, Agent, or Firm*—Brian C. Carey; Briana C. Bergen

(57) ABSTRACT

The present invention relates to methods of screening drug candidates for toxic effects on human cells. The invention provides methods for determining idiosyncratic toxicity of test compounds.

16 Claims, 6 Drawing Sheets

Controls

◆ Perhexiline $IC_{50}$ < 20 µM (positive control)
◆ Theophylline $IC_{50}$ > 694 µM (negative control)
◆ Interplate variation coefficient < 10%

| | Perhexiline | | | | |
|---|---|---|---|---|---|
| Molarity | Tc5 | 3A4 | 2C9 | 2C19 | 2D6 |
| 0.000 | 100 | 100 | 100 | 100 | 100 |
| 0.004 | 93.8 | 92.2 | 95.1 | 102.8 | 93.9 |
| 0.008 | 90.2 | 46.5 | 94.9 | 100.8 | 101.6 |
| 0.016 | 10.5 | 4.6 | 36.9 | 33.5 | 69.5 |
| 0.032 | 0.9 | 0.9 | 1.0 | 0.7 | 0.9 |
| 0.064 | 1.0 | 0.9 | 0.7 | 0.6 | 1.2 |
| IC50 (µM) | 11 | 7 | 13 | 13 | 19 |

| | Theophylline | | | | |
|---|---|---|---|---|---|
| Molarity | Tc5 | 3A4 | 2C9 | 2C19 | 2D6 |
| 0.000 | 100 | 100 | 100 | 100 | 100 |
| 0.043 | 92.1 | 95.8 | 94.9 | 95.0 | 94.5 |
| 0.087 | 96.4 | 92.8 | 95.9 | 92.9 | 93.8 |
| 0.173 | 92.6 | 97.6 | 95.7 | 93.7 | 95.7 |
| 0.347 | 91.6 | 94.5 | 96.5 | 89.5 | 93.7 |
| 0.694 | 89.0 | 90.6 | 90.8 | 90.9 | 91.0 |
| IC50 (µM) | >694 | >694 | >694 | >694 | >694 |

METHODS OF SCREENING FOR TOXICITY OF TEST COMPOUNDS

This application claims priority from U.S. Provisional Application Ser. No. 60/336,509 filed on Oct. 31, 2001, which is incorporated herein by reference in its entirety.

FIELD OF THE INVENTION

The invention relates to methods of screening test compounds to determine their effect on cells. In particular, the present invention relates to methods of screening potential drug candidates for toxic effects on human cells.

BACKGROUND OF THE INVENTION

Human cell lines have been used in a variety of laboratory applications. For example, immortalized human liver cells have been used in metabolic studies with different chemical classes of carcinogens. Bronchial epithelial cells have been used in studies of the control of squamous differentiation, and identification of chemical and biological agents which induce squamous differentiation. Both of these human cell types have been used in screening chemicals suitable for the treatment of cancer and related diseases, by growing them in vitro in medium containing the chemical to be tested and then, after a suitable period of exposure, determining whether and to what extent genotoxicity, DNA adduct formation, mutagenicity, cell transformation and/or cytotoxicity has occurred following exposure to a carcinogen, e.g., by trypan blue exclusion assay or related assays. These cell lines have also been used for identifying agents that induce programmed cell death or apoptosis, which may have an important impact on prevention of malignant transformation. Programmed cell death is assayed by DNA fragmentation or cell-surface antigen analysis.

Human cell lines have also been used to study DNA mutagenesis. Substances known or suspected to be mutagens, or precursors of mutagens, may be added to the growth medium of the cells and then mutations may be assayed, e.g., by detection of the appearance of drug resistant mutant cell colonies. Similarly, cell-mediated DNA mutagenesis has been investigated by co-cultivating the cells with cell types known or suspected to be capable of secreting mutagenic compounds. Human cell lines have also been used in studies of chromosome damaging agents, studies of malignant transformation, screening for potential chemotherapeutic agents, studies of cellular biochemistry, studies of cellular responses to growth factors and production of growth factors, studies of intracellular communication, characterization of cell surface antigens, hybrid studies for identification of tumor suppressor activity, and identification of novel genes.

In all of the aforementioned studies, the human cell lines used are capable of expressing a cytochrome P450. Cytochromes P450 are a large family of hemoprotein enzymes capable of metabolizing xenobiotics such as drugs, carcinogens and environmental pollutants as well as endobiotics such as steroids, fatty acids and prostaglandins. Some members of the cytochrome P450 family are inducible in both animals and cultured cells, while other constitutive forms are non-inducible. This group of enzymes has both harmful activities, such as the metabolic conversion of xenobiotics to toxic, mutagenic and carcinogenic forms, and beneficial activities, such as the detoxification of xenobiotics.

In the pharmaceutical industry, screening drug candidate compounds for toxicity is a critical step in the drug development process. It is highly desirable to identify, as early as possible, compounds that have an increased likelihood of toxicity. For example, liver toxicity, such as acute liver failure, is currently the leading cause of drug removal from the market.

Chemical injury to the liver is a multi-faceted phenomenon involving factors such as the nature of the toxic agent, the mechanisms of injury, the nature of the exposure and the susceptibility of the host. A variety of agents can lead to hepatic damage, but in general compounds that are able to injure the liver of most recipients in a variety of species are called "true" or "intrinsic" liver toxicants. Agents that depend on unusual susceptibility of the host to unmask their damaging potential are called "idiosyncratic" hepatotoxins. This increased sensitivity of the host's liver to the damaging effects of the chemical can be linked to two broad categories of mechanisms. The first category is accompanied by clinical and physiological symptoms suggesting the involvement of an immune response and is usually designated as "drug hypersensitivity." The second category consists of liver damage appearing in the absence of concomitant immune reaction, and has been called "metabolic idiosyncrasy" (Zimmerman, H., Hepatoxicity, $2^{nd}$ ed., Lippincott, Williams & Wilkins, Philadelphia, Pa. (1999)). The hypothesis underlying the "metabolic idiosyncrasy" theory is that some products of drug metabolism are responsible for the damage done to the liver cells, but that those metabolites are not produced in sufficient quantities in the majority of the population to result in overt hepatic injury. In some patients, however, the metabolic pathway of the drug favors the production of a toxic species, resulting in liver injury.

There are many obstacles to predicting metabolite-related liver toxicity of pharmaceuticals. Prediction of liver toxicity in clinical trials is poor due to a number of factors, including high polymorphism in the population, differences in metabolism between animal models and humans, and differences in cytochrome P450 expression due to gender and age. In addition, in vivo studies are expensive and time-consuming.

One of the major obstacles in the drug development process is predicting which drug candidates will exhibit idiosyncratic toxicity. A major challenge in predicting metabolic idiosyncrasy is not to find models that are representative of the majority of the population, but rather to find models that are representative of those few subjects for which the metabolism is oriented toward toxicity. As compared to intrinsic toxicity, idiosyncratic toxicity is far more difficult to predict, due to the nature of the toxicity. Intrinsic toxicity is: (1) typically a property of the drug; (2) a constant occurrence; (3) dose-dependent; (4) characterized by a clear onset of toxicity; and (5) predicted by animal models. Idiosyncratic toxicity, on the other hand, is: (1) typically a result of interaction between the drug and patient specific factors; (2) a relatively rare occurrence (<1/10,000); (3) usually independent of dose; (4) characterized by a delayed onset; and (5) difficult (if not impossible) to predict with animal models.

Thus, there is a need for rapid, affordable, accurate methods of screening compounds for toxicity. Specifically, there is a need for methods to predict idiosyncratic toxicity of a drug candidate. In particular, there is a need for methods to identify idiosyncratic toxicity early in the drug development process. There is also a need for methods of screening compounds for toxicity which reflect human metabolism and are representative of the diverse human population.

SUMMARY OF THE INVENTION

The present invention features methods of screening a compound to determine the toxic effect of the compound on cells. In one aspect, the invention provides a method of determining whether a compound exhibits idiosyncratic toxicity by contacting a test compound with a cell which expresses a Phase I enzyme, contacting the cell with a cell viability indicator to determine whether the test compound has generated a toxic metabolite, wherein generation of a toxic metabolite indicates that the test compound exhibits idiosyncratic toxicity. In a preferred embodiment, the indicator is a chromogenic compound, more preferably, a tertazolium compound, and most preferably, the indicator is 3-(4,5-dimethylthiazol-2-yl)-5-(3-carboxymethoxyphenyl)-2-(4-sulfophenyl)-2H-tetrazolium, inner salt). The most preferred cell line used in the method of the invention is the THLE-5B cell line (also referred to as "THLE-5"). Preferred cytochromes P450 include 3A4, 2C9, 2C19, 2D6, 1A1, 1A2, 2B6, 2C11 and 2E1. Of these, 3A4, 2C9, 2C19, and 2D6 are the most preferred cytochromes P450 for use with the invention.

The methods of the invention may be performed manually. Preferably, the methods of the invention are performed using an automated system to achieve high throughput.

DETAILED DESCRIPTION OF THE INVENTION

In one aspect the present invention takes advantage of the metabolization of chemical compounds by liver cells. Generally speaking, the elimination of a chemical compound by the liver usually involves two steps. In the first step, some portion of the compound's chemical structure is modified to form a "chemically-reactive" end. In the second step, a large, hydrophilic group is added to that reactive portion to disrupt the three-dimensional structure of the parent compound and facilitate its elimination in biological fluids. These steps form the two "phases" of drug metabolism, and are each catalyzed by specific families of enzymes. Cytochromes P450 are among the enzymes responsible for "Phase I" reactions, or the formation of a reactive entity.

In some cases, there may be a desynchronization between the production of reactive species by the phase one enzyme reactions, and subsequent elimination by conjugation during phase two. For example, desynchronization occurs when there is an increase in the amount of Phase I enzymes, causing an increase in reactive metabolites, but no corresponding increase in Phase II enzymes. Alternatively, desynchronization may result from an absence or depletion of Phase II enzymes, such as results from polymorphism. However, depletion of Phase II enzymes may also occur in subjects who are treated with an additional substance, such as a blood-thinning compound or an herbal supplement. In these subjects, metabolites of the additional substance may compete for the Phase II enzyme that otherwise would be present to act on the reactive metabolites formed by the Phase I enzymes. As a result of desynchronization, reactive species may accumulate inside the cytoplasm and may bind to macromolecules, i.e., proteins, involved in cell structure or metabolism. The alteration of these macromolecules may result in the loss of critical functions and cellular toxicity.

Figure 1:
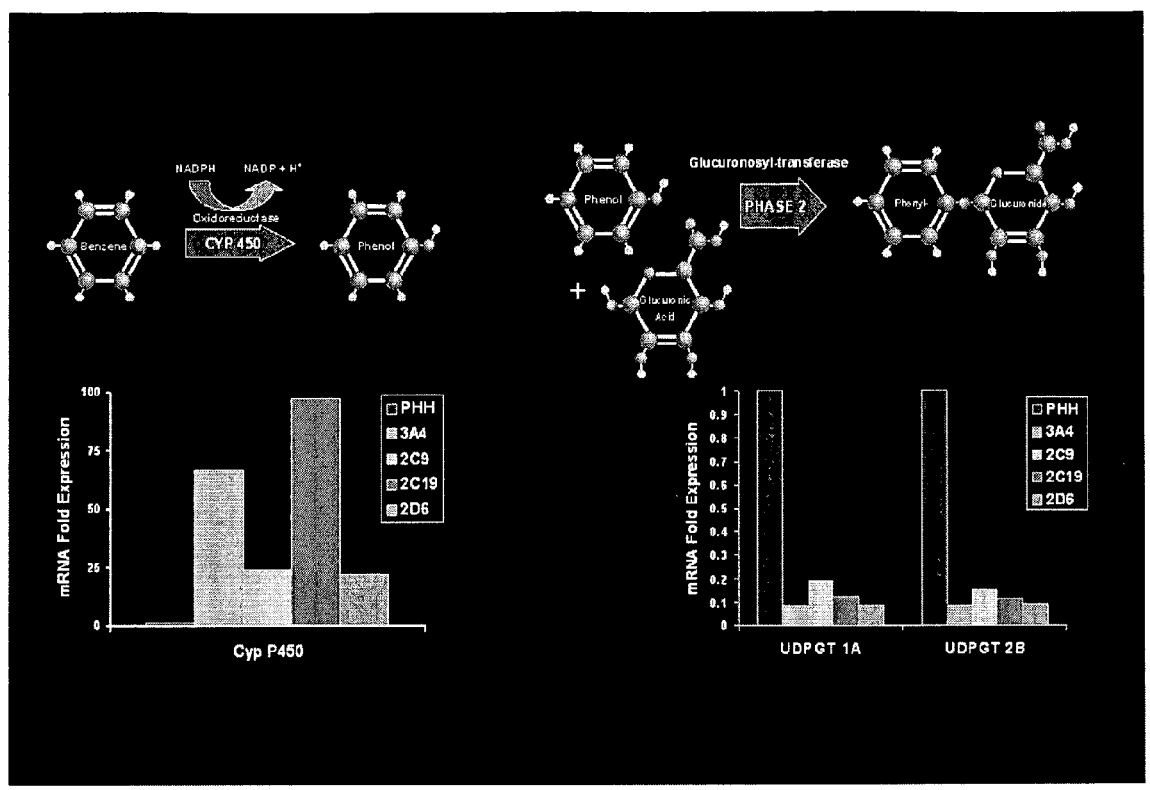
FIG. 1 is a graphical representation of mRNA expression levels in THLE-5 cells for key Phase I (left) and Phase II (right) enzymes, as compared to primary human hepatocytes (PHH).

In one embodiment, the present invention provides a method of screening chemical compounds for toxicity by increasing the amount of Phase I enzymes of a specific type, while taking advantage of a reduction in the Phase II enzyme production in the host cells (See FIG. 1). In a preferred embodiment, the amount of Phase I enzymes in a cell is increased through the use of an expression vector. According to the method of the invention, the transfected cells have a vastly increased potential to generate reactive metabolites directly in their cytoplasm and demonstrate any toxic effect. In this manner, the method of the invention simulates conditions that may arise in the liver of individuals who are susceptible to idiosyncratic toxicity. In a preferred embodiment, the method of the invention includes a cell having increased expression levels of a Phase I enzyme. For example, increased expression of a Phase I enzyme is at least about 20 fold more, more preferably at least about 50 fold more, and most preferably, at least about 100 fold more than expression of the same enzyme in primary human hepatocytes (PHH). In another preferred embodiment, the method of the invention includes a cell having decreased expression of a Phase II enzyme. For example, decreased expression of a Phase II enzyme is at least about 70%, more preferably at least about 80%, and most preferably, at least about 90% less than expression of the same enzyme in PHH.

In general, any cell line that expresses or is made to express a cytochrome P450 may be used in the invention. Cell lines derived from human liver parenchymal cells are preferred for the prediction of hepatotoxicity. Immortalized human cell lines for use in the method of the invention may be obtained through methods known in the art. For example, human hepatocyte cell lines may be immortalized by transformation with simian virus 40 large T antigen, as described in Pfeifer, A. M., et al., "Simian virus 40 large tumor antigen-immortalized normal human liver epithelial cells express hepatocyte characteristics and metabolize chemical carcinogens," *Proc. Natl. Acad. Sci. U.S.A.* 90, 5123–5127 (1993), hereby incorporated by reference in its entirety.

The immortalized human cells are reported to be similar to quiescent normal human hepatocytes, are non-tumorigenic when injected into nude mice, have near-diploid karyotypes, do not express alpha-fetoprotein, and are free of Hepatitis B or human immunodeficiency virus (Pfeifer et al, 1993). The THLE-5 cell line (also sometimes referred to as "THLE-5B") was deposited under the terms and conditions of the Budapest Treaty at the American Type Culture Collection on Apr. 23, 1992, and was assigned the accession number CRL11113. The parent cell line, THLE-5B-c15 (T5-c15) does not express Phase I metabolizing activity, but retains normal expression of most Phase II metabolizing enzymes, such as glutathione S-transferase, epoxide hydrolase, N-acetyl transferase type I, aldehyde reductase, and quinone reductase, as well as detoxification systems, such as superoxide dismutase (SOD) and catalase.

In a preferred embodiment, multiple cells, each expressing a different cytochrome P450, are used in the method of the invention. Four separate cell lines, THLE-5B-3A4, THLE-5B-2C9, THLE-5B-2C19, and THLE-5B-2D6, expressing the different cytochrome P450s indicated by their names (3A4, 2C9, 2C19, and 2D6, respectively), were derived by transfection of THLE-5B-c15 with a plasmid containing a CMV expression vector, human cDNA coding for the specific P450 isoenzyme and a selection marker, using methods known in the art.

The use of these four cell lines allows for the determination of the specific role of each of these enzymes in the generation of toxic metabolites or detoxification of a parent compound. Thus, in another embodiment of the present invention, information gathered by this method of the invention may be used to predict the likelihood of toxicity in particular population groups. For example, detoxification of a parent compound by CYP 2D6 only may be shown by a decrease in cell viability with increased drug concentration in the parent TC5 cell line and three other daughter lines, but not in the 2D6 cell line. These results suggest, in a population that is deficient in this enzyme, an increased likelihood of hepatic liability.

The invention is based, in part, on the effect cytochrome P450 polymorphism can have on drug metabolism. Six isoenzymes of cytochrome P450 (2E1, 2C19, 2C9, 3A4, 2D6, 1A1, and 1A2) account for about 95% of all cytochrome P450-mediated reactions. Of these, 2D6, 2C9, and 2C19 are the cytochromes P450 that account for the majority of polymorphism associated with clinically relevant changes in drug effects. See Evans, W. E. and Relling, M. V., "Pharmacogenomics: translating functional genomics into rational therapeutics," *Science* 286(5439): 487–91 (Oct. 15, 1999).

FIG. 1 depicts mRNA expression levels for key Phase I (left) and Phase II (right) enzymes, as compared to primary human hepatocytes (PHH). In FIG. 1, the level of expression of the metabolism enzymes have been normalized to the level of expression of the same enzyme in primary human hepatocytes. As shown on the left graph, the cells express many fold more mRNA of the respective P450 than primary human hepatocytes. In addition, phase II enzymes, such as UDPGT, are approximately 10 fold less expressed. This differential expression enhances the formation of potential reactive metabolites as well as their ability to react with critical cellular components.

Figure 2:
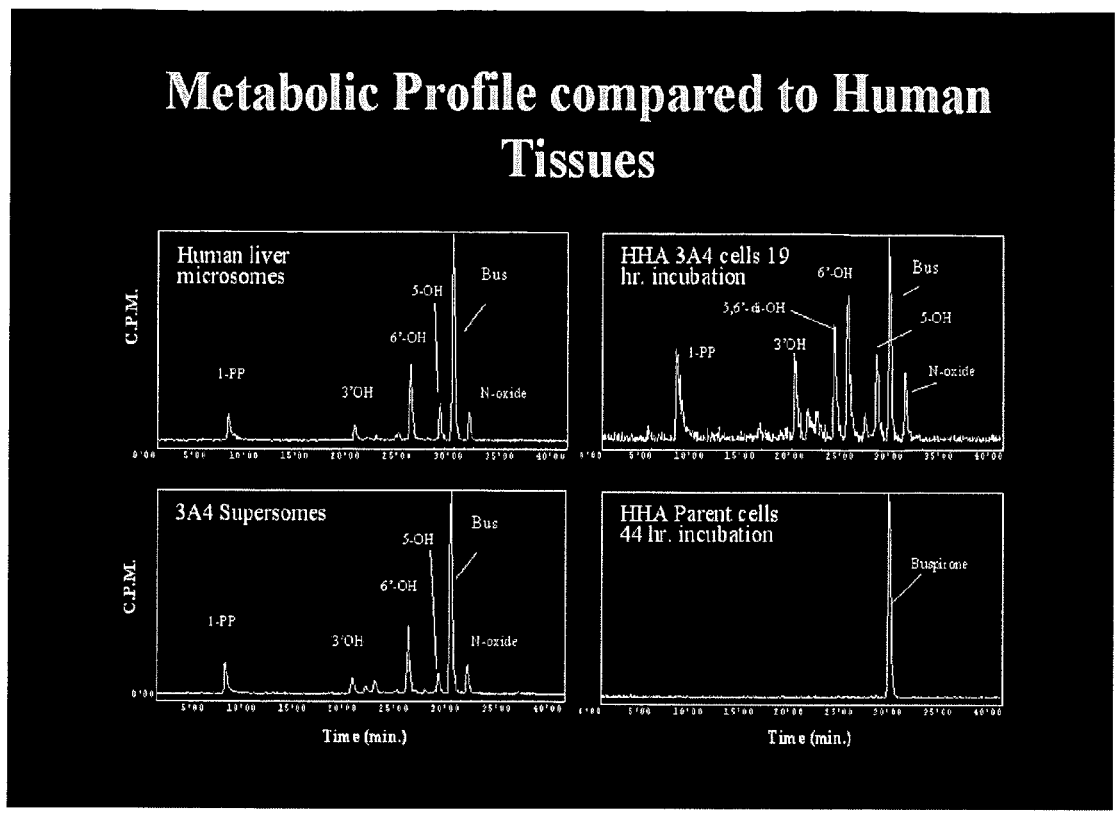
FIG. 2 is a graphical comparison of the metabolism of buspirone by human liver microsomes, 3A4 Supersomes®, 3A4 and TC5 cell lines.

FIG. 2 compares the metabolism of buspirone by human liver microsomes, 3A4 Supersomes®, 3A4, and TC5 cell lines. The metabolic profile of the 3A4 cell line closely matches the results obtained with microsomes extracted from human livers or insect cell line, demonstrating that metabolites produced in the testing system are very likely to be also produced in a subject's liver. As expected, the parent cell line does not show any metabolism of the test compound even after 44 hours incubation.

Figure 3:
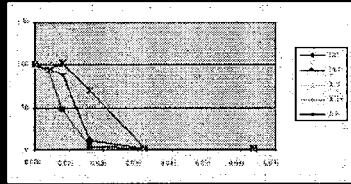
FIG. 3 shows the results for control samples used in a high throughput assay of the invention.
Figure 3:
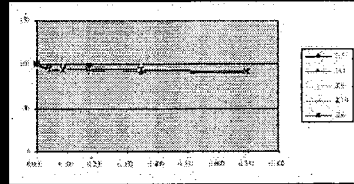

FIG. 3 shows the results for control samples used in a high throughput assay of the invention. Cell-only and media-only controls may be included on every plate. In addition, two compounds, e.g., perhexiline (positive control of toxicity—known human liver toxicant) and theophylline (negative control of toxicity) may be included in each test. The interplate variation coefficient is calculated from cell-only and media-only wells present on each plate.

Figure 4:
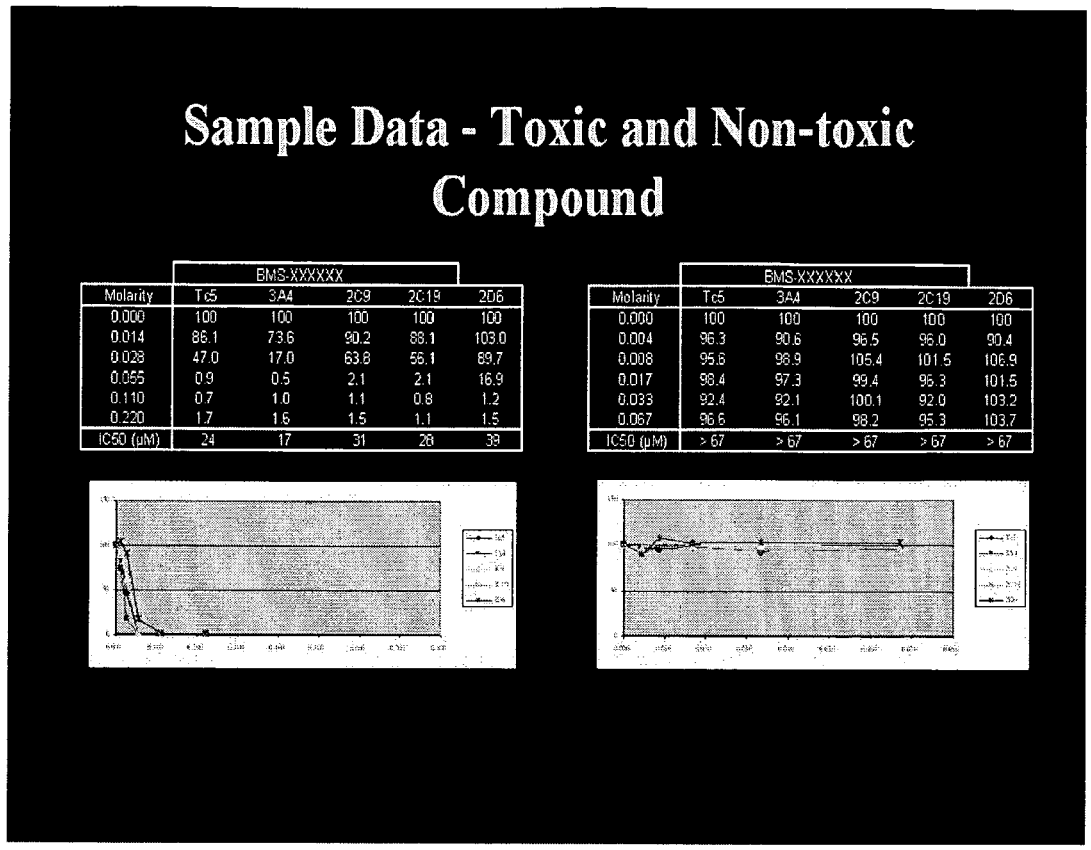
FIG. 4 depicts sample data obtained from a method of the invention.

FIG. 4 depicts sample data obtained from a method of the invention. The compound on the left exhibited toxicity in the TC5 cell line as well as all the transfected cell lines. It is therefore predicted to be an intrinsic liver toxicant. The compound on the right is not predicted to have increased likelihood of clinical liver liability.

Figure 5:
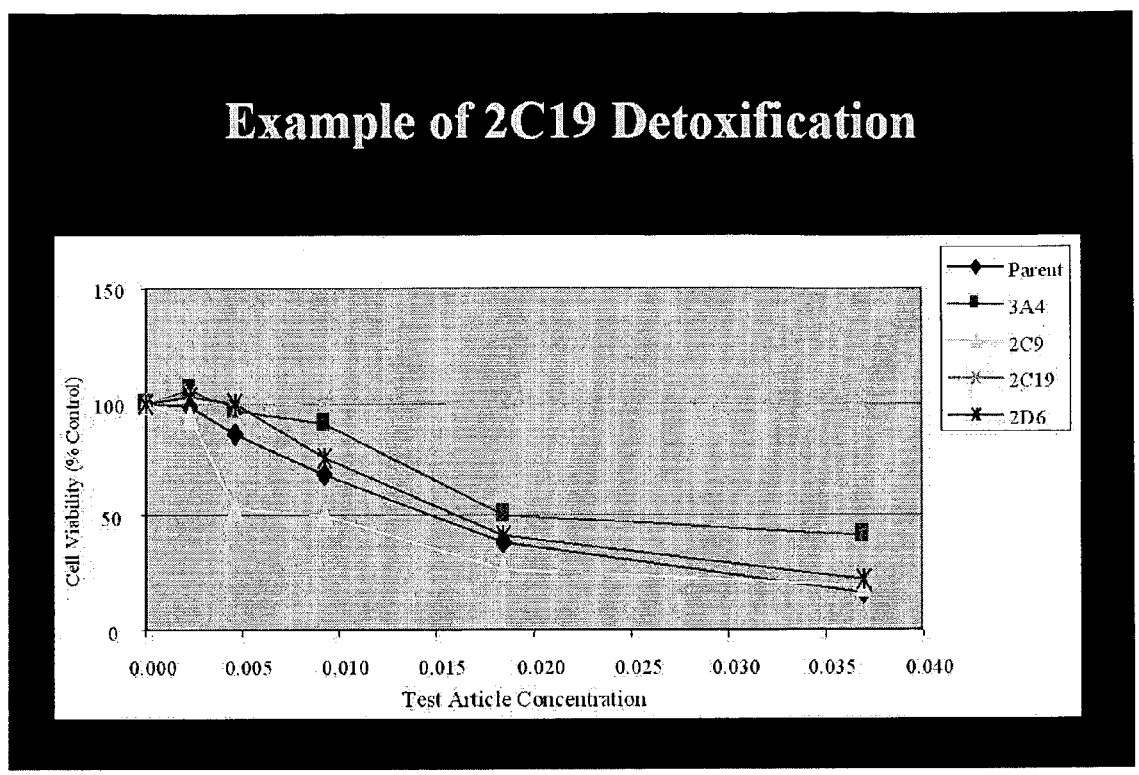
FIG. 5 demonstrates reduced toxicity of a parent compound by CYP 2C19 metabolism.

FIG. 5 demonstrates reduced toxicity of a parent compound by CYP 2C19 metabolism. The assay shows a marked amelioration of the parent compound toxicity following metabolism by cytochrome P450 2C19. This compound might be harmless for a majority of the population. However, increased liver toxicity may appear in the subpopulation of poor CYP 2C19 metabolizers.

Figure 6:
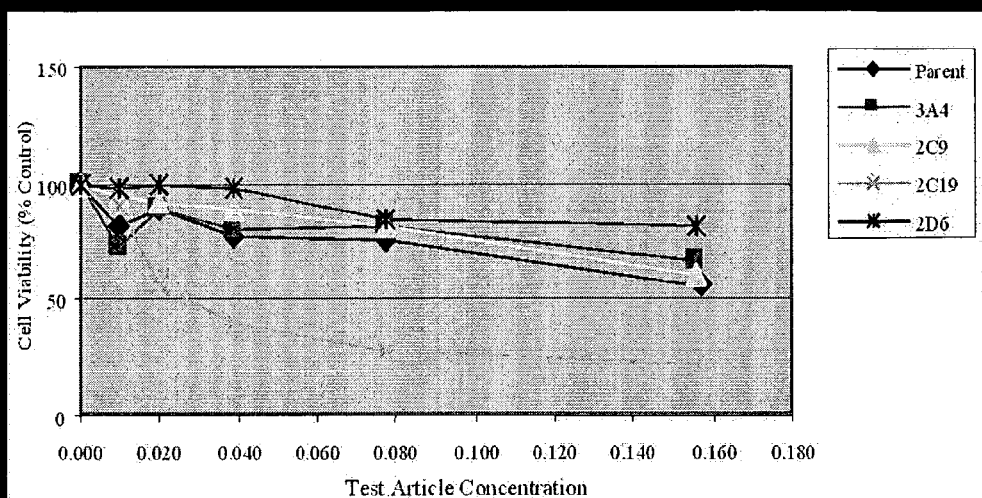
FIG. 6 shows increased toxicity following CYP 2C19 metabolism.

FIG. 6 demonstrates increased toxicity following CYP 2C19 metabolism. In such a case, it might be helpful to test the compound on primary human hepatocytes to assess the importance of the 2C19 route in the overall metabolism of the drug candidate.

The following solutions and reagents were prepared and used in the experiments described herein.

Culture Medium (CM)

Low calcium medium, PMFR-4, supplemented with 2 mM L-glutamine, 50 µg/mL gentamycin, 1.75 µM insulin, 0.2 µM hydrocortisone, 5 ng/mL epidermal growth factor, 10 µg/mL transferrin, 500 nM phosphoryethanolamine/ethanolamine, 50 nM trliodothyronine, 15 µg/mL bovine pituitary extract, 0.33 nM retinoic acid, and 3% fetal bovine serum (Biofluids).

Trypsin EDTA 1× (0.05%), Life Technologies.

Solutions of 3-(4,5-dimethylthiazol-2-yl)-5-(3-carboxymethoxyphenyl)-2-(4-sulfophenyl)-2H-tetrazolium, inner salt ("MTS") and phenazine methosulfate (PMS) were prepared as follows. Because the MTS solution is light sensitive, it was prepared fresh for each run of the assay.

MTS Solution

A 2 mg/mL MTS solution was prepared by dissolving 240 mg MTS (Promega Corp.) powder in 120 mL of Dulbecco's PBS ($Ca^{2+}$, $Mg^{2+}$ free, Life Technologies). The solution was warmed as necessary to dissolve the powder, then filtered through a 0.22 µm filter.

PMS Solution

A 0.92 mg/mL solution of phenazine methosulfate (PMS, Sigma) in PBS was prepared and filtered through a 0.22 µm filter.

The two solutions are combined at a ratio of 20 ml of MTS to 1 ml of PMS for use.

Coating Media

To 500 mL of LHC basal medium (Biofluids, #118) was added human fibronectin 5 mg (Collaborative Biomedical Products, #40008A), Vitrogen 100 (purified bovine collagen) 5 mL (Collagen Corp #PC0701), BSA stock 0.1%, 50 mL, (Biofluids #343). The solution was filtered through a 0.22 µm filter.

A sufficient amount of coating medium is added to cover the well or flask, followed by incubation for at least for 15 minutes at 37° C. Coating media was removed prior to seeding flask or well.

Cell Preparation and Culture

Cells were grown at 37° C., under 5% $CO_2$. The cells were serially passaged in 175 $cm^2$ culture flasks, split 1:10, every 7 days. Approximately every 5th passage, cells were selected by addition of 150 µg/ml of G418. Periodically, metabolic activity of the daughter lines were verified by usage of P450-specific fluorescent substrates. For cell passage, the cells were rinsed with PBS, incubated 5 minutes with trypsin (trypsin EDTA 1× (0.05%), Life Technologies), and harvested in culture medium. For experimental treatments, cells were seeded at $1.5 \times 10^4$ cells/well in 96-well culture dishes (Falcon) in a 100 µL volume.

Test Compound Preparation and Administration

All test compounds were dissolved in DMSO at 25 mg/mL (25,000 µg/mL) and 5 mg/mL (5,000 µg/mL), which was added to the culture medium to a final concentration of 1% (v/v). Before testing, starting concentrations of 250 and 50 µg/mL were read in a SPECTRAmax™ spectrophotometer at 450 nm to evaluate the solubility. If a compound was not soluble at 50 µg/mL, serial dilutions were prepared and tested to determine the highest soluble concentration. For testing in the robotic system, the initial concentration in the mother plate was 250 µg/mL or 50 µg/mL (2× concentration). These two starting concentrations will produce overlapping curves. The first dilution and highest concentration tested was 125 µg/mL or 25 µg/mL in 0.5% DMSO and the final volume was 100 µL. The further serial dilutions were 2-fold, 62.5, 31.25, 15.6, and 7.8 µg/mL (12.5, 6.25, 3.125, 1.625 µg/mL) and the DMSO was diluted 2-fold in the same pattern. Culture medium containing test compound (100 µL) was added to the cells after a confluent monolayer had formed. Positive (e.g. perhexiline) and negative (e.g. theophylline) reference agents were included in each test.

In the automated or "robotic" procedure, a "mother plate" (96-well) containing test articles in triplicate at twice the highest concentration to be tested (25 mg/mL), served as the supply of compounds for the assay. From this mother plate, five successive 2-fold serial dilutions (100 µL) were made, using the robotic arm (CRS Robotics, Burlington, Ontario) and Quadra pipettor for each cell line. For example, a compound made at a concentration of 200 µM into the mother plate would be tested on the cells in plate 1 at 100 µM, at 50 µM in plate 2, at 25 µM in plate 3, at 12.5 µM in plate 4 and at 6.25 µM in plate 5. These 5 different concentrations would be repeated for each of the 5 cell lines, for a total of 25 different plates. The plates were incubated in a Hotpack incubator at 37° C. under 5% $CO_2$ for 20 hrs. Following the incubation period, 22 µL of the combined PMS-MTS solution was added using the robotic arm and Quadra pipettor. The test plates were again transferred to the incubator. After an additional 2 hr incubation with MTS, the plates were individually transported to a plate reader (Wallac Victor 1420) and absorbance intensity was measured at 490 nm.

In the manual procedure, test compounds at twice the highest concentration to be tested, served as the supply of compounds for the assay. From this mother plate, five successive 2-fold serial dilutions were made for each cell line. For example, a compound made at a concentration of 200 µM into the mother plate would be tested on the cells in plate 1 at 100 µM, at 50 µM in plate 2, at 25 µM in plate 3, at 12.5 µM in plate 4 and at 6.25 µM in plate 5. These 5 different concentrations are repeated for each of the 5 cell lines, for a total of 25 different plates. A hand-held multi-pipettor was used to perform the steps in the manual assay. The plates were incubated at 37° C. under 5% $CO_2$ for 20 hrs in a standard laboratory incubator. Following the incubation period, 22 µL of the combined PMS-MTS solution were added to each well. After an additional 2 hr incubation, absorbance intensity was measured at 490 nm using a Wallac Victor 1420 plate reader.

Cell Viability Assessment

MTS is an indicator of mitochondrial function. The assay is thus a calorimetric method for determining the number of viable cells in proliferation. MTS, in the presence of an electron coupling reagent (phenazine methosulfate), is bioreduced by cells into a formazan that is soluble in tissue culture medium. The conversion of MTS into the aqueous soluble formazan is accomplished by dehydrogenase enzymes found in metabolically active cells. The quantity of formazan product as measured by the amount of absorbance at 490 nm is directly proportional to the number of metabolically active cells in culture.

Analysis of Results

Validation of the run was made by comparing three criteria (perhexiline $IC_{50}$, theophylline $IC_{50}$ and plate-to-plate coefficient of variation) with historical references. If a test was rejected, then all data from this particular run were discarded and all test articles were rerun. Data from validated tests were adjusted for background absorbance (defined by the "medium-only wells) as well as plate-to-plate variability, expressed as percentage of the viability observed in the cell-only wells and examined for significant concentration-related changes with respect to the endpoint measured. For each replicate of the test compound, concentration-response curves were plotted for the different cell lines and an $IC_{50}$ determined using a four-parameters logistic regression model. The $IC_{50}$ is defined as the concentration corresponding to a 50% viability on the regression line. A mean and standard deviation (SD) is calculated from the three IC50 obtained from the replicates. These data are reported for each test compound, as well as positive and negative controls.

Interpretation of Results

For compounds with maximum solubility greater than 50 µM.

Test compounds with an $IC_{50}$ in any of the cell lines less than 50+SD were predicted to have an increased likelihood of clinical hepatic liabilities. Test compounds with an $IC_{50}$ in all cell lines greater than 50+SD µM were predicted to have a reduced likelihood of clinical hepatic liabilities.

For compounds with maximum solubility less than 50 µM

Test compounds with an $IC_{50}$ in any of the cell lines were predicted to have an increased likelihood of clinical hepatic liabilities. If the dose response curve allows extrapolation to 50 µM, test articles with an extrapolated $IC_{50}$ in all cell lines greater than 50+SD µM were predicted to have a reduced likelihood of clinical hepatic liabilities and test articles with an extrapolated $IC_{50}$ less than 50 µM in any of the cell lines were predicted to have an increased likelihood of clinical hepatic liabilities. If the maximum solubility reached in the assay does not allow extrapolation to 50 µM, the likelihood of clinical hepatic liabilities cannot be predicted.

EXAMPLES

Example 1

Immortalized human hepatocytes were plated at $1.5 \times 10^4$ cells per well in 100 µL culture media on coated plates. These cells were incubated overnight at 37° C. under 5% $CO_2$. A confluent monolayer formed during this incubation. Cells were exposed to test compounds by adding 100 µL of test compound to cells at 2× the concentration to be tested. Serial dilutions were made for lower concentrations (1 concentration per plate). Cells were then incubated at 37° C. under 5% $CO_2$ for 20 hrs. MTS reagent was added in 22 µL volume to each well. Cells were then incubated for 2 hrs, and the absorbance at 490 nm was determined.

All publications, patents, and patent applications mentioned in this specification are herein incorporated by reference to the same extent as if each independent publication, patent, or patent application was specifically and individually indicated to be incorporated by reference.

What is claimed is:

1. A method of determining whether a compound exhibits idiosyncratic toxicity comprising:
   a) contacting a test compound with at least one first cell line which expresses a Phase I enzyme and with a second cell line which does not express a Phase I enzyme;
   b) contacting the first and second cell lines with a cell viability indicator to determine whether the first cell line has generated a toxic metabolite from said test compound; and
   c) observing for any reduction in cell viability of the first cell line relative to the second cell line, wherein a greater reduction of cell viability of the first cell line relative to the cell viability of the second cell line is indicative of the generation of the toxic metabolite and that the test compound exhibits idiosyncratic toxicity.

2. The method of claim 1, wherein the first cell line is THLE-5B-3A4, THLE-5B-2C9, THLE-5B-2C19, or THLE-5B-2D6.

3. The method of claim 1, wherein the Phase I enzyme is a cytochrome P450.

4. The method of claim 3, wherein the cytochrome P450 is 3A4, 2C9, 2C19, 2D6, 1A1, 1A2, 2B6, 2C11 or 2E1.

5. The method of claim 1, further comprising a plurality of first cell lines wherein each cell line expresses a different Phase I enzyme.

6. The method of claim 5, wherein the plurality of cell lines comprises THLE-5B-3A4, THLE-5B-2C9, THLE-5B-2C19, and THLE-5B-2D6.

7. The method of claim 1, wherein the indicator is 3-(4,5-dimethylthiazol-2-yl)-5-(3-carboxymethoxyphenyl)-2-(4-sulfophenyl)-2H-tetrazolium, inner salt.

8. The method of claim 1, wherein the cell line expresses the Phase I enzyme at a level that is at least about 20 fold more than the level of expression of the Phase I enzyme in primary human hepatocytes.

9. The method of claim 1, wherein the cell line expresses the Phase I enzyme at a level that is at least about 50 fold more than the level of expression of the Phase I enzyme in primary human hepatocytes.

10. The method of claim 1, wherein the cell line expresses the Phase I enzyme at a level that is at least about 100 fold more than the level of expression of the Phase I enzyme in primary human hepatocytes.

11. The method of claim 1, wherein the cell line expresses a Phase II enzyme at a level that is at least about 70% less than the level of expression of the Phase II enzyme in primary human hepatocytes.

12. The method of claim 1, wherein the cell line expresses a Phase II enzyme at a level that is at least about 80% less than the level of expression of the Phase II enzyme in primary human hepatocytes.

13. The method of claim 1, wherein the cell line expresses a Phase II enzyme at a level that is at least about 90% less than the level of expression of the Phase II enzyme in primary human hepatocytes.

14. A method of determining whether a compound exhibits idiosyncratic toxicity comprising:
   a) contacting a test compound with a first cell line which expresses a cytochrome P-450 enzyme and with a second cell line which does not express a cytochrome P-450 enzyme;
   b) contacting the first and second cell lines with a cell viability indicator to determine whether the first cell line has generated a toxic metabolite from said test compound; and
   c) observing for any reduction in cell viability of the first cell line relative to the second cell line, wherein a greater reduction of cell viability of the first cell line relative to the cell viability of the second cell line is indicative of the generation of the toxic metabolite and that the test compound exhibits idiosyncratic toxicity.

15. A method of determining idiosyncratic toxicity of a compound comprising:
   a) contacting a test compound with a plurality of first cell lines and with a second cell line which does not express a Phase I enzyme, each first cell line expressing a different Phase I enzyme;
   b) contacting the first and second cell lines with a cell viability indicator to determine whether any of the first cell lines has generated a toxic metabolite from said test compound; and
   c) observing for any reduction in cell viability of the first cell lines relative to the second cell line wherein a reduction of cell viability in any of the first cell lines relative to the second cell line is indicative of the generation of the toxic metabolite and that the test compound exhibits idiosyncratic toxicity.

16. A method for determining the likelihood of hepatic liability in a population following administration of a test compound comprising:
   a) contacting a test compound with a plurality of first cell lines and with a second cell line which does not express a cytochrome P-450 enzyme, each first cell line expressing a different cytochrome P-450 enzyme;
   b) contacting the first and second cell lines with a cell viability indicator to determine whether any of the first cell lines has generated a toxic metabolite from said test compound; and
   c) observing for any changes in viability of the first cell lines relative to the viability of the second cell line, wherein greater cell viability found for any of the first cell lines relative to the second cell line is indicative that a population deficient in the cytochrome P-450 enzyme expressed by any of the first cell lines having greater cell viability after test compound contact has a likelihood of hepatic liability following administration of the test compound to the population.

* * * * *